(12) United States Patent
Wouters et al.

(10) Patent No.: US 9,877,812 B2
(45) Date of Patent: Jan. 30, 2018

(54) VIRTUAL SPLINT

(71) Applicant: NOBEL BIOCARE SERVICES AG, Kloten (CH)

(72) Inventors: Veerle Wouters, Kessel-lo (BE); Wouter Mollemans, Antwerp (BE); Filip Schutyser, Sint-Niklaas (BE); Pascal Kunz, Zurich-Airport (CH)

(73) Assignee: Nobel Biocare Services AG, Kloten (CH)

( * ) Notice: Subject to any disclaimer, the term of this patent is extended or adjusted under 35 U.S.C. 154(b) by 254 days.

(21) Appl. No.: 14/427,239

(22) PCT Filed: Aug. 26, 2013

(86) PCT No.: PCT/EP2013/002556
§ 371 (c)(1),
(2) Date: Mar. 10, 2015

(87) PCT Pub. No.: WO2014/040696
PCT Pub. Date: Mar. 20, 2014

(65) Prior Publication Data
US 2015/0238290 A1     Aug. 27, 2015

(30) Foreign Application Priority Data
Sep. 12, 2012  (GB) .................................. 1216224.4

(51) Int. Cl.
*A61C 13/00*       (2006.01)
*B29C 67/00*       (2017.01)
(Continued)

(52) U.S. Cl.
CPC .......... *A61C 13/0004* (2013.01); *A61C 1/084* (2013.01); *B29C 67/0088* (2013.01);
(Continued)

(58) Field of Classification Search
CPC ..... A61C 13/0004; A61C 1/084; A61C 5/007; A61C 9/004; A61B 17/176; A61B 2017/00526; A61F 5/566
(Continued)

(56) References Cited

U.S. PATENT DOCUMENTS

| 5,015,183 A | 5/1991 | Fenick |
| 5,133,660 A | 7/1992 | Fenick |

(Continued)

FOREIGN PATENT DOCUMENTS

| EP | 1 043 960 131 | 9/2003 |
| EP | 1 486 900 | 12/2004 |

(Continued)

OTHER PUBLICATIONS

Fortin, T. et al., "Dental Implant, Computer Assisted Surgical Guide," Engineering in Medicine and Biology Society, Proceedings of the 15th Annual International Conference of the IEEE, 1993, pp. 1617-1618.
(Continued)

*Primary Examiner* — Kimberly A Williams
(74) *Attorney, Agent, or Firm* — Knobbe, Martens, Olson & Bear LLP

(57) ABSTRACT

In embodiment of the invention provides a method of producing a dental splint comprising the steps of: obtaining a set of 3D surface data, the 3D surface data representing a surface of a patient's oral situation, obtaining a support structure model describing a dental splint configured to fit to a portion of the surface of the patient's oral situation, modifying an apical edge of the support structure model in dependence on the 3D surface data, producing the dental splint in dependence on the modified support structure model.

14 Claims, 18 Drawing Sheets

(51) Int. Cl.
*G05B 15/02* (2006.01)
*G06F 17/50* (2006.01)
*A61C 1/08* (2006.01)
*B33Y 50/02* (2015.01)

(52) U.S. Cl.
CPC ............. *G05B 15/02* (2013.01); *G06F 17/50* (2013.01); *B33Y 50/02* (2014.12)

(58) Field of Classification Search
USPC ........................................................ 345/420
See application file for complete search history.

(56) References Cited

U.S. PATENT DOCUMENTS

| | | |
|---|---|---|
| 5,320,529 A | 6/1994 | Pomba |
| 5,718,579 A | 2/1998 | Kennedy |
| 5,725,736 A | 3/1998 | Schroeder et al. |
| 5,743,916 A | 4/1998 | Greenberg et al. |
| 5,768,134 A | 6/1998 | Swaelens et al. |
| 5,772,437 A | 6/1998 | Rangert et al. |
| 6,053,920 A | 4/2000 | Carlsson et al. |
| 6,902,401 B2 | 6/2005 | Jorneus et al. |
| 7,175,435 B2 | 2/2007 | Andersson et al. |
| 7,572,125 B2 | 8/2009 | Brajnovic |
| 7,792,341 B2 | 9/2010 | Schutyser |
| 7,846,357 B2 | 12/2010 | Johansson |
| 7,942,668 B2 | 5/2011 | Brajnovic et al. |
| 7,950,924 B2 | 5/2011 | Brajnovic et al. |
| RE43,584 E | 8/2012 | Andersson et al. |
| 8,425,229 B2 | 4/2013 | Nilsson et al. |
| 8,428,315 B2 | 4/2013 | Suetens et al. |
| 8,824,764 B2 | 9/2014 | Mollemans et al. |
| 9,095,377 B2 | 8/2015 | Karlsson et al. |
| 2002/0150859 A1 | 10/2002 | Imgrund et al. |
| 2003/0065259 A1 | 4/2003 | Gateno et al. |
| 2004/0175671 A1 | 9/2004 | Jones et al. |
| 2005/0140670 A1 | 6/2005 | Wu et al. |
| 2007/0197902 A1 | 8/2007 | Schutyser |
| 2008/0118895 A1 | 5/2008 | Brajnovic |
| 2008/0159608 A1 | 7/2008 | Suetens et al. |
| 2008/0182220 A1* | 7/2008 | Chishti .................... A61C 7/00 433/24 |
| 2008/0248443 A1* | 10/2008 | Chishti .................... A61C 7/00 433/24 |
| 2009/0187393 A1 | 7/2009 | Van Lierde et al. |
| 2009/0239197 A1 | 9/2009 | Brajnovic |
| 2009/0248184 A1 | 10/2009 | Steingart et al. |
| 2009/0263764 A1 | 10/2009 | Berckmans et al. |
| 2009/0311647 A1 | 12/2009 | Fang et al. |
| 2009/0325122 A1 | 12/2009 | Brajnovic et al. |
| 2009/0325127 A1 | 12/2009 | Kusch et al. |
| 2011/0059413 A1 | 3/2011 | Schutyser et al. |
| 2011/0275032 A1 | 11/2011 | Tardieu |
| 2012/0046914 A1 | 2/2012 | Gao |
| 2012/0100500 A1 | 4/2012 | Gao |
| 2012/0201443 A1 | 8/2012 | Mollemans et al. |
| 2012/0214121 A1 | 8/2012 | Greenberg |
| 2013/0289950 A1* | 10/2013 | Kopelman ........... A61C 8/0001 703/1 |
| 2015/0238289 A1 | 8/2015 | Wouters et al. |
| 2015/0245890 A1 | 9/2015 | Wouters et al. |
| 2015/0265374 A1 | 9/2015 | Masoud |
| 2015/0327958 A1 | 11/2015 | Llop et al. |
| 2016/0213442 A1* | 7/2016 | Geier .................... A61B 6/145 |

FOREIGN PATENT DOCUMENTS

| | | |
|---|---|---|
| EP | 1 364 625 B1 | 5/2007 |
| FR | 2 898 485 A1 | 9/2007 |
| WO | WO 94/15545 | 7/1994 |
| WO | WO 95/03007 | 2/1995 |
| WO | WO 95/15731 | 6/1995 |
| WO | WO 96/01083 | 1/1996 |
| WO | WO 97/43981 | 11/1997 |
| WO | WO00/69357 | 11/2000 |
| WO | WO 2007/035326 | 3/2007 |
| WO | WO 2008/043056 | 4/2008 |
| WO | WO 2009/094576 | 7/2009 |
| WO | WO 2011/101447 | 8/2011 |
| WO | WO 2014/040695 | 3/2014 |
| WO | WO 2014/040697 | 3/2014 |
| WO | WO 2014/108332 | 7/2014 |
| WO | WO 2014/127908 | 8/2014 |

OTHER PUBLICATIONS

Fortin, T. et al., "Computer-Assisted Dental Implant Surgery Using Computed Tomography," J. of Image Guided Surgery, 1995, 1:53-58.

Israelson, H. et al., "Barium-Coated Surgical Stents and Computer Assisted Tomography in the Preoperative Assessment of Dental Implant Patients," the International Journal of Periodontics & Restorative Dentistry, vol. 12, No. 1, 1992. pp. 52-61.

Sethi, Ashok, "Precise Site Location for Implants Using CT Scans: a Technical Note," the International Journal of Oral & Maxillofacial Implants, vol. 8, No. 4, 1993, pp. 433-438.

International Search Report for Application No. PCT/EP2013/002555 dated Dec. 5, 2013 in 4 pages [the ISR for the PCT Application of U.S. Appl. No. 14/427,202].

International Search Report for Application No. PCT/EP2013/002556 dated Jan. 8, 2014 in 4 pages (the ISR for the PCT Application of this US national phase application).

International Search Report for Application No. PCT/EP2013/002557 dated Dec. 2, 2013 in 4 pages [the ISR for the PCT Application of U.S. Appl. No. 14/427,219].

* cited by examiner

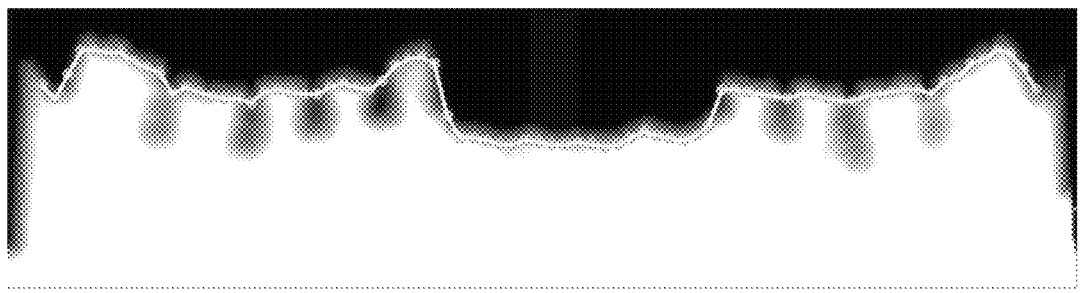
Figure 7a
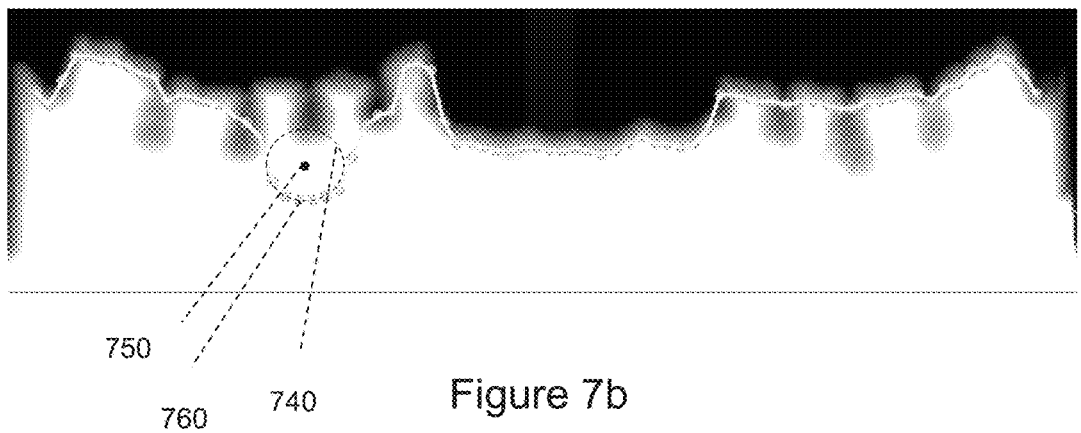
750
760   740   Figure 7b
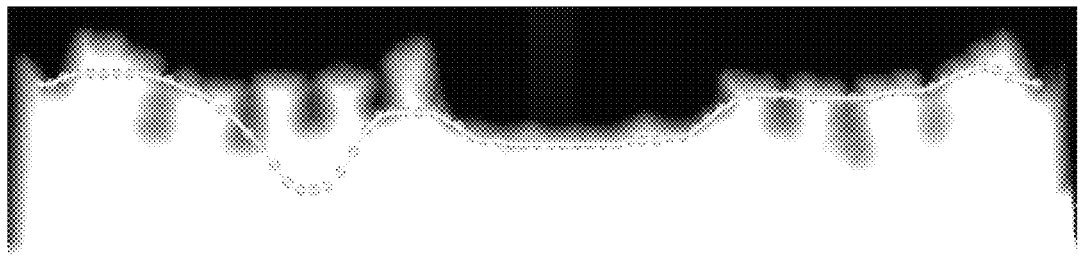
Figure 7c

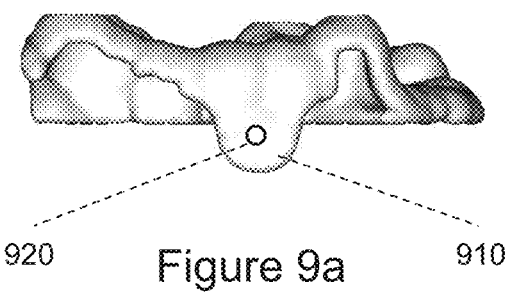
920  Figure 9a  910
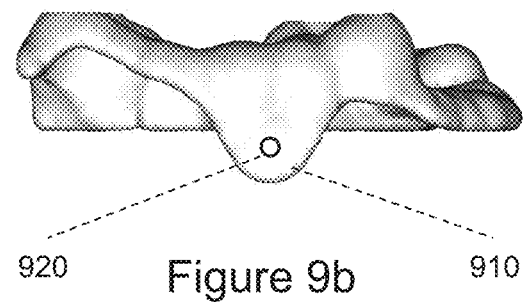
920  Figure 9b  910

VIRTUAL SPLINT

CROSS-REFERENCE TO RELATED APPLICATIONS

This application is a national stage application under 35 U.S.C. § 371 of International Application No. PCT/EP2013/002556, filed on Aug. 26, 2013, which published in English as WO 2014/040696 A1 on Mar. 20, 2014 and which claims priority benefit of GB Patent Application No. 1216224.4 filed on Sep. 12, 2012.

FIELD

This invention relates in general to the field of cranial surgery, including dentistry. More particularly the invention relates to a method and apparatus for producing dental splints or occlusal splint used to protect teeth, such as night guards or sports guards, or to be used by a surgeon to facilitate and guide the installation of oral implants or guide other oral surgeries, such as maxillofacial surgeries.

BACKGROUND

An example of a treatment workflow using guided surgery methods for the installation of oral implants in a patient is provided:
1. The dentist examines the patient and may acquire an X-ray image or scan of the patient's oral situation.
2. An impression of the oral situation is taken and used to produce a plaster model of the patient's jawbone and teeth.
3. A teeth setup, modeling the position, size and shape of a desired prosthesis, is created on the plaster model and then fitted to the patient. It is then adjusted and optimized to match the patient's oral situation and clinical needs.
4. Based on the teeth setup, a radiographic guide is produced. The radiographic guide contains radio-opaque markers and is configured to be fitted to the patient. A bite index is also created, which fits between the radiographic guide and the opposing jaw of the patient, holding the radiographic guide in the mouth of the patient in the correct position.
5. A double-scan procedure is then used to image the patient's oral situation. The patient is scanned first with the radiographic guide and bite index in position using a CT scanner. The radiographic guide is then scanned alone. From the first scan, a computer model of the patient is generated. From the second scan, a computer model of the radiographic guide is generated. Both models are then aligned to one another using the landmarks in the CT data resulting from the radio-opaque markers. This allows a detailed representation of the patient's oral situation to be provided on a computer, including soft tissue surface contours (i.e. intaglio surface of radiographic guide), alongside CT data showing bone and nerve structures.
6. The position and orientation of the implants is planned using the computer representation (comprising the surface detail and CT data) of the patient's oral situation. Similarly, the position of any required anchor pins is also planned at this stage.
7. A dental splint (also known, in this case, as a surgical template) is produced having the same shape as the radiographic guide, but containing drill holes at the position of the planned implants and anchor pins. Each drill hole is provided with a metal sleeve.
8. The dental splint is placed in the patient's mouth and used to guide the drilling and the placement of the dental implants in the patient's jawbone.

There are several known problems with this treatment workflow.

Firstly, in order to produce the surgical template, a radiographic guide must be produced first. The production of a radiographic guide is usually not done by the surgeon himself, but by a lab specializing in the production of dental components. This makes the treatment workflow more complex and slower due to transportation. The production of the radiographic guide is also time consuming and expensive.

Secondly, as the patient has usually already been scanned at an early stage (see step 1 above), the scan with the radiographic guide further raises the radiation dose of the patient. Furthermore, if the radiographic guide is not fitted correctly to the patient during the scanning procedure, a rescan must be performed, further increasing the radiation dose.

Although the oral surgeon may choose to avoid these extra expenses and complications by installing the implants in a conventional way without the use of a computer modeling and planning, the improved accuracy and predictability of the modern treatment workflow is lost. In reality, few surgeons are likely to choose this option.

Therefore, what is needed is a modern treatment workflow for producing a dental splint for guided oral surgery or other uses which avoids the need for a radiographic guide.

SUMMARY

An embodiment of the invention provides a method of producing a dental splint comprising the steps of: obtaining a set of 3D surface data, the 3D surface data representing a surface of a patient's oral situation, obtaining a support structure model describing a component configured to fit to a portion of the surface of the patient's oral situation, modifying an apical edge of the support structure model in dependence on the 3D surface data, producing the dental splint in dependence on the modified support structure model.

FIGURES

Aspects of the present invention will now be described by way of example with reference to the accompanying drawing. In the drawings:

FIG. 7a shows a panoramic maximum intensity projection of a distance map image of a second patient with a cut-off line.

FIG. 7b shows the cut-off line of FIG. 7a further lowered around a planned anchor pin site.

FIG. 7c shows the cut-off line of FIG. 7b after smoothing.

FIG. 9a shows a rendered support structure model for the second patient with the applied cut-off line of FIG. 7b.

FIG. 9b shows a rendered support structure model for the second patient with the applied cut-off line of FIG. 7c.

DESCRIPTION OF EMBODIMENTS

Figure 1A:
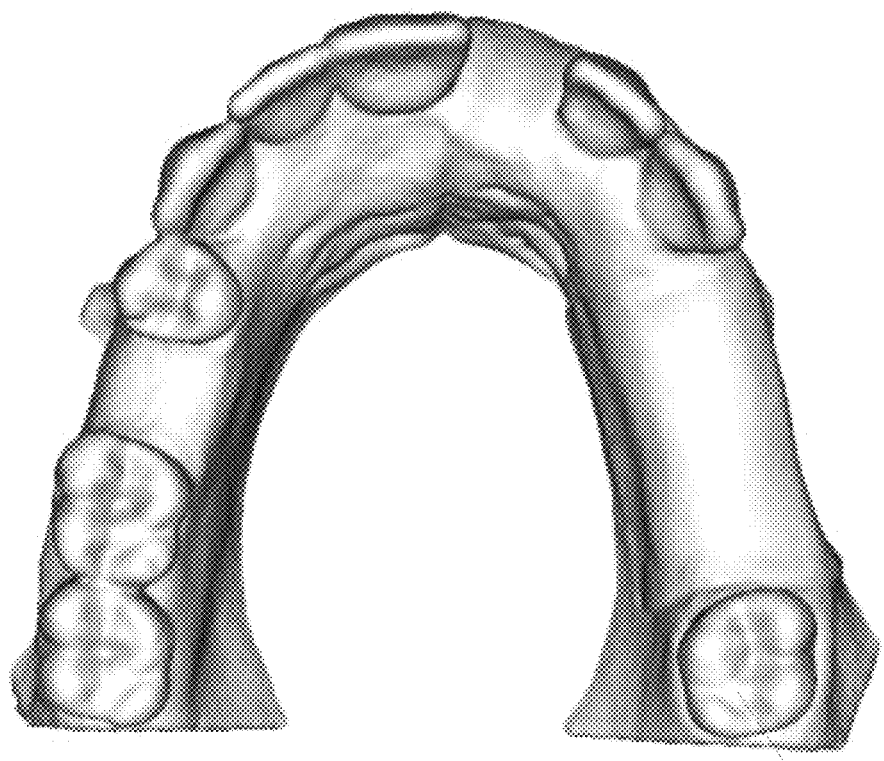
FIG. 1a shows a 3D surface model of the patient's oral situation.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to surgical templates for guiding the installation of oral implants. However, it will be appreciated that the invention is not limited to the use of surgical templates, but may be applied to the production of dental splints, e.g. protective mouth guards or other similar applications.

The following is a description of a preferred embodiment of the invention, which is a method of producing a surgical template without the use of a radiographic guide. The same technique can be used to produce a range of dental splint types. Firstly, a set of 3D surface data describing the surface of a patient's oral situation is obtained. Secondly, a virtual surgical template model is generated in dependence on the 3D surface data and the planned implant and anchor pin positions. Thirdly, a physical surgical template is produced from the virtual surgical template model.

Determination of Patient's Oral Situation

The surface of the patient's oral situation is typically the upper or lower occlusal dental arch of the patient, including the soft tissue and teeth on the buccal, occlusal and lingual sides.

The 3D surface data of the patient's oral situation may be obtained using a number of known optical or radiographic imaging techniques. For example, an intra-oral optical scanner used on the patient's mouth would produce 3D surface data suitable for use with this method. Alternative methods include: an optical scan of an impression of the patient's oral situation (processed as required to compensate for the impression being a negative imprint of the oral situation), an optical scan of a die-cast model of the patient's oral situation, a high-resolution 3D X-ray computed tomography (CT) or magnetic resonance imaging (MRI) image of the oral situation combined with a surface detection algorithm.

Both the intra-oral optical scan and the optical or tactile scan of an impression or die-cast model have the advantage of minimal radiation exposure for the patient and high resolution surface scanning. The CT and MRI scanners provide the advantage of visualizing the internal anatomical structures as well.

The present invention can be used for guided implant placement using: a digital model based approach without CT data, a digital model based approach fused with CT data or just a CT/MRI image combined with a surface detection algorithm.

Figure 1B:
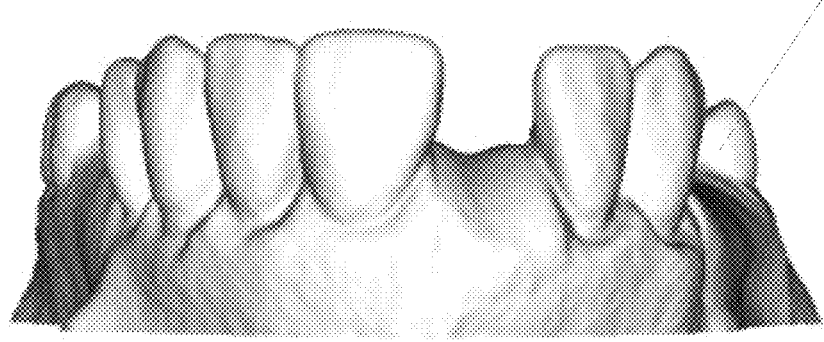
FIG. 1b shows the 3D surface model of FIG. 1a from a second perspective.

The 3D surface data 110 of the patient's oral situation is preferable stored as vertices and triangles describing the triangulated surface shown in FIGS. 1a and 1b.

Generating the Support Structure Model

A number of techniques may be used to generate the virtual surgical template model from the 3D surface data of the patient's oral situation. A virtual support structure model may be used as an intermediate step in this process.

Preferably, a distance map imaging method is used to process the 3D surface data to form a virtual surgical template model.

Figure 2A:
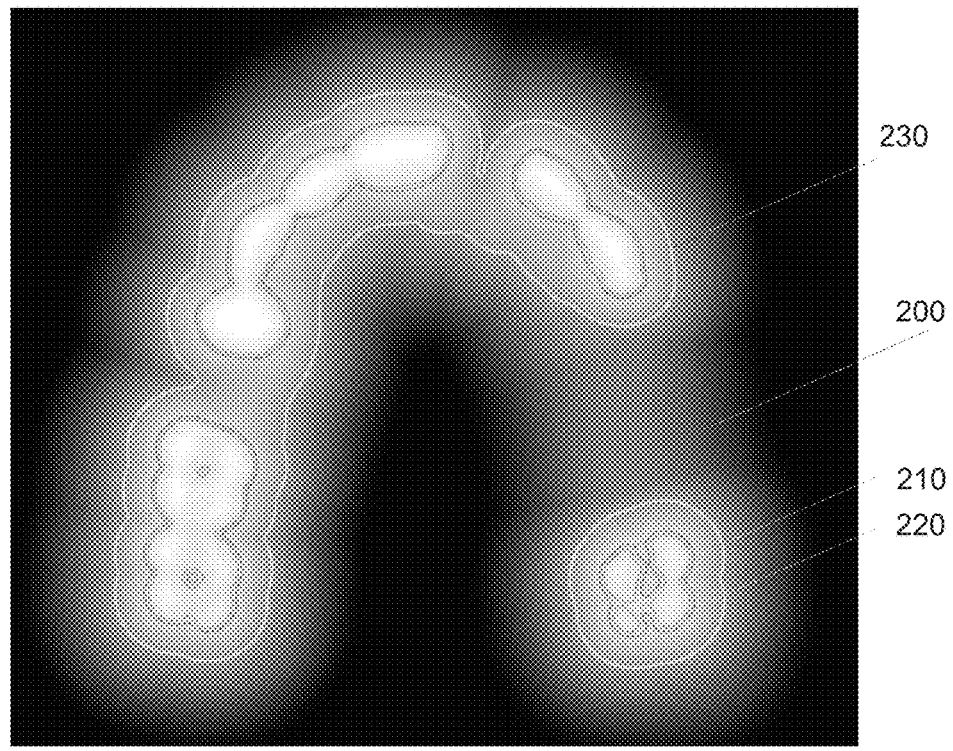
FIG. 2a shows a horizontal slice of a distance map of the 3D surface data of the patient's oral situation.
Figure 2B:
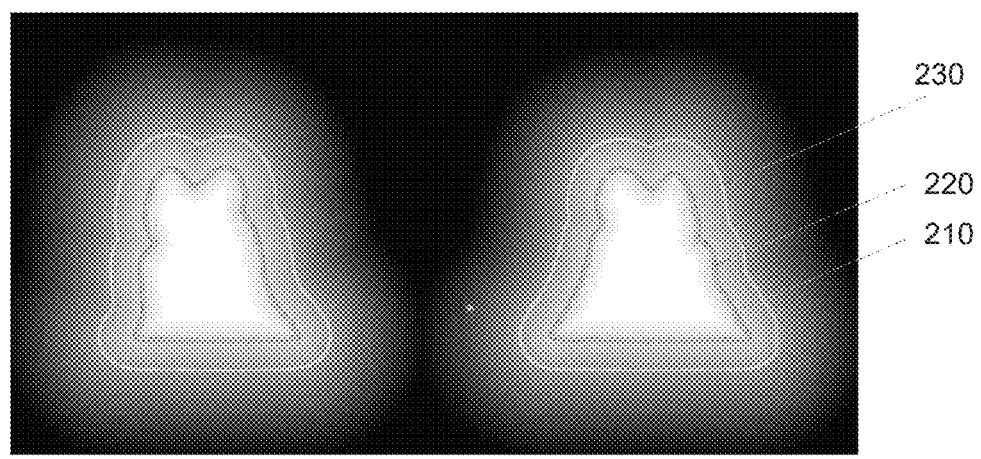
FIG. 2b shows a coronal slice (left-right cross-sectional) of the 3D surface data of the patient's oral situation

The 3D surface data of the patient's oral situation is processed to form a 3D distance map image 200. This is done by starting from an empty voxel image having the same frame of reference as the 3D surface described by the 3D surface data. Each voxel of the distance map image is assigned a value corresponding to the minimum distance of the voxel to the 3D surface described by the 3D surface data. FIG. 2a shows a horizontal slice of a distance map of the patient's oral situation and an outline of the 3D surface 210. FIG. 2b shows a coronal slice of a distance map of the patient's oral situation and an outline of the 3D surface 210.

In one embodiment, for the lower jaw, voxels at the 3D surface or below (i.e within the volume of the 3D surface data which represents the patient's tissues) are assigned a positive value. Voxels that are above the 3D surface are assigned a negative value. The further the voxel lies from the 3D surface, the greater the value (negative or positive) assigned to the voxel. Other embodiments may comprise alternative voxel value configurations.

Once the distance map image is generated, a support structure model is generated comprising all the voxels having a value within a particular range of the distance map image. In one embodiment, all voxels having a value (and thus a particular distance from the 3D surface) between a first value, representing a position close to the 3D surface, and a second value greater than the first value in magnitude, representing a position further away from the 3D surface, are selected to form the support structure. The first value is chosen to select a distance from the 3D surface where the surface of the support structure model begins. The second value is chosen to define the thickness of the support structure, wherein the thickness is dependent on the difference between the first and second values. The resulting support structure model matches the 3D surface and will fit the patient's oral situation. A larger first value provides a larger tolerance between the 3D surface and the support structure. A small amount of play is provided by the tolerance. In a preferred embodiment, the tolerance is between 0.1 mm and 0.5 mm. FIGS. 2a and 2b show an outline for the first value 220 and the second value 230.

Figure 3A:
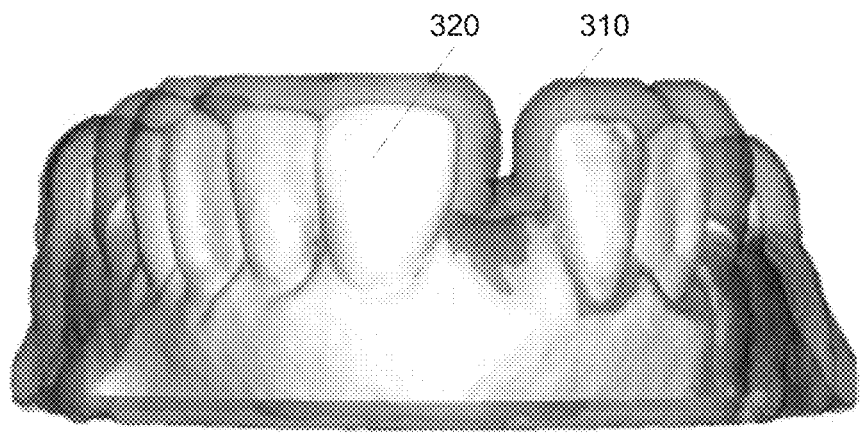
FIG. 3a shows a transparent support structure model and the 3D surface model of FIG. 1b beneath.
Figure 3B:
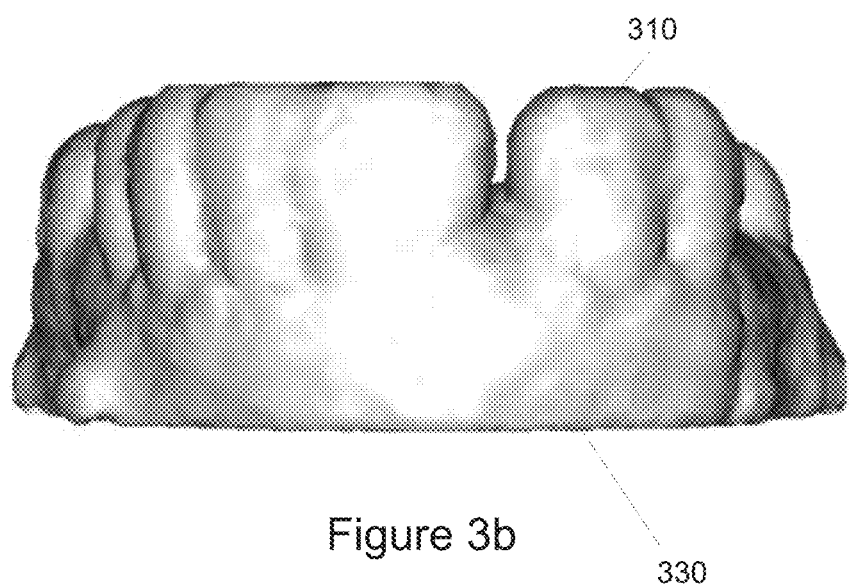
FIG. 3b shows the support structure model of FIG. 3a without any transparency.

In one embodiment, the first and second values are chosen to generate a support structure model containing all voxels with a distance between 0.1 and 2.1 mm above the 3D surface. The resulting support structure model will have a consistent thickness of 2.0 mm. FIGS. 3a and 3b show an embodiment of the support structure model 310 overlying the 3D surface 320 of the patient's oral situation. The support structure model 310 has an apical edge 330. In FIG. 3a, the support structure model is shown partly transparent in order to see the 3D surface beneath.

The advantage of generating a support structure model automatically in this way is that it is accurate and computationally robust to produce. Given just the 3D surface data of the patient's oral situation, a matching support structure model can be produced quickly and accurately using this technique.

Figure 4:
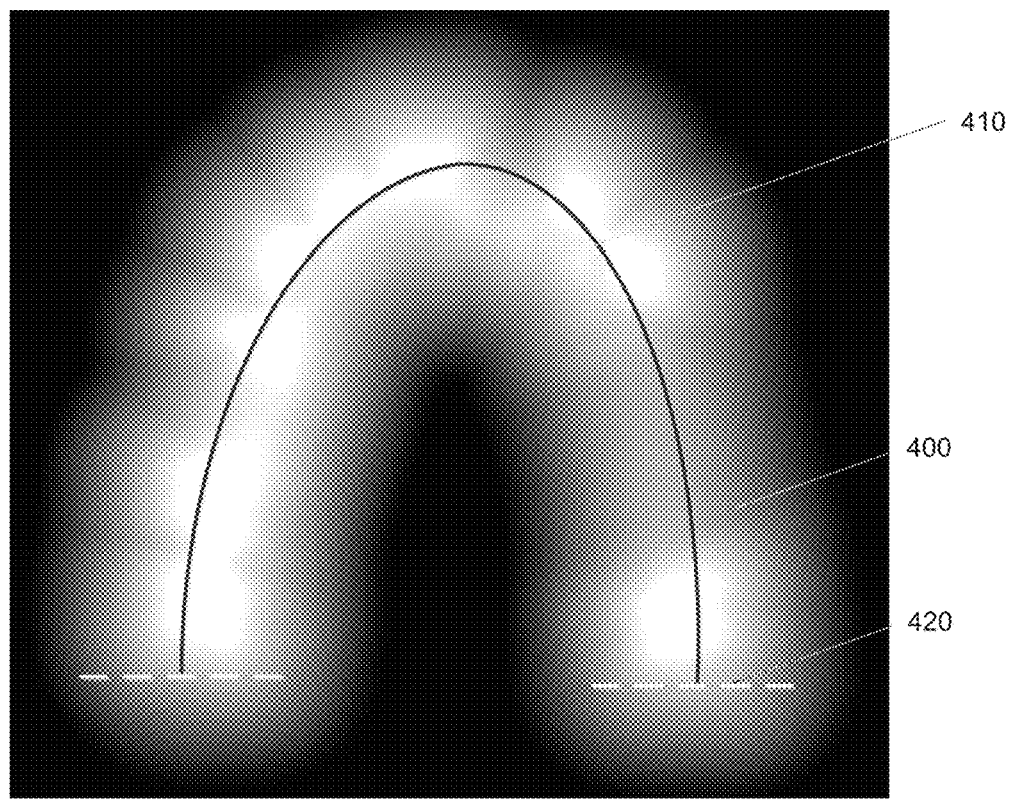
FIG. 4 shows a horizontal slice of a distance map of the 3D surface data of the patient's oral situation including an indication of the dental arc.

The support structure model should also be limited along the dental arc so that it does not stretch all the way up to the molar teeth at the back of the patient's mouth. Instead, a rearward limit is defined. In FIG. 4, limit line 420 shows the rearward or posterior limit of the support structure model along the dental arc.

In an alternative embodiment, a subtractive technique is used to generate the virtual surgical template model from the 3D surface data of the patient's oral situation. In this technique, a predefined shape having a shape approximating a dental splint is provided. Any shape larger than the oral situation of the patient and still small enough to be used as a support structure model would be suitable. The predefined shape is overlaid onto the 3D surface so that they overlap. A boolean operation is then performed to subtract the 3D surface of the 3D surface data from the predefined shape. The resulting shape has the same general shape as the predefined shape but with a surface matching the 3D surface. This resultant shape would be a suitable basis for a support structure.

In another alternative embodiment, a dilation technique is used to generate the virtual surgical template model from the 3D surface data of the patient's oral situation. This comprises the step of creating a binary image of the 3D surface, wherein the voxels inside the 3D surface have a value of 1 and the voxels outside the 3D surface have a value of 0. The resultant image is then dilated to produce an enlarged binary image of the 3D surface. The original binary 3D surface is then subtracted from the enlarged image to form a resultant support structure, having a thickness dependent on the degree to which the dilated image was enlarged over the 3D surface.

In another alternative embodiment, a z-transfer technique is used to generate the virtual surgical template model from the 3D surface data of the patient's oral situation. This comprises using a model of the 3D surface overlaid with a second model of the 3D surface data shifted in the Z-axis. The geometric space between the two 3D Surfaces can then be used to form the support structure. This provides a support structure model with a surface matching the patient's oral situation and having a consistent thickness.

Customizing the Support Structure Model

According to the preferred embodiment of the invention, once the support structure model has been generated, it may be further refined to include specific characteristics or features.

As the finalized surgical template will be produced from the support structure model, any changes to the characteristics of the support structure model will also result in changed characteristics of the final surgical template.

Support Structure Model Cut-Off Line

Figure 5A:
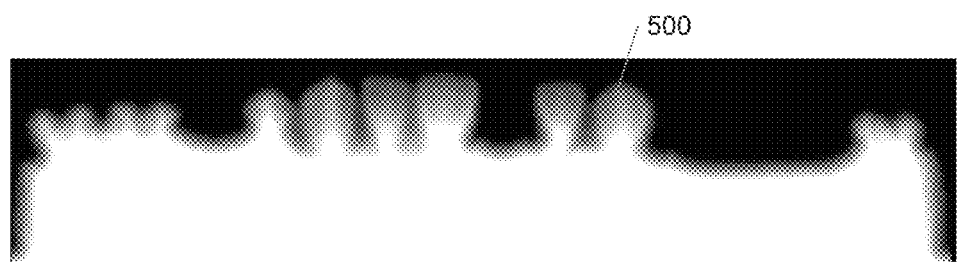
FIG. 5a shows a panoramic maximum intensity projection of a distance map image.
Figure 5B:
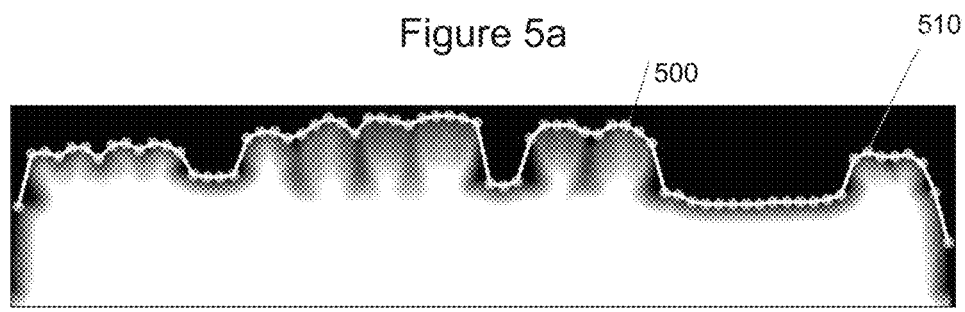
FIG. 5b shows FIG. 5a with a high point line, delineating the upper edge of the 3D surface model.
Figure 5C:
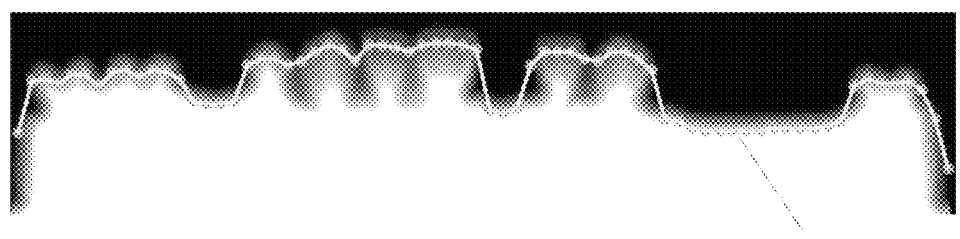
FIG. 5c shows the high point line of FIG. 5b lowered by a distance to form a cut-off line to be used on the buccal side of the support structure.

In the preferred embodiment, the support structure model is configured to cover just a coronal portion of the patient's existing teeth or gum surfaces. A cut-off line limiting the support structure model in the apical direction is used. This is achieved in the following way:

1. First, as shown in FIG. 4, a dental arc 410 is determined relative to the distance map image 400. In an alternative embodiment, the arc is determined according to the 3D surface data of the patient's oral situation. In another embodiment, the arc is indicated by the user.
2. Then, a maximum intensity projection of the distance map image 400 is generated along the arc 410, forming a panoramic image shown in FIG. 5a of a lower jaw similar to an orthopantomogram typically used by dentists. Ridge 500 is clearly visible.
3. As shown in FIG. 5b, the highest points (or coronal edge) along the top of ridge 500 are recorded, forming a line 510 defining the upper boundary of the 3D surface data. The highest points are determined as the transition point from the pixels indicating teeth material to the pixels indicating empty space (e.g. the transition between negative and positive values) at each vertical line of the panoramic image.
4. Line 510 is then lowered (away from the occlusal plane) in FIG. 5c. This new line defines the buccal cut-off line 520 of the support structure model along arc 410. For an equivalent upper jaw, the line 510 is raised (also away from the occlusal plane) instead of lowered to form the cut-off line 520.

Figure 5D:
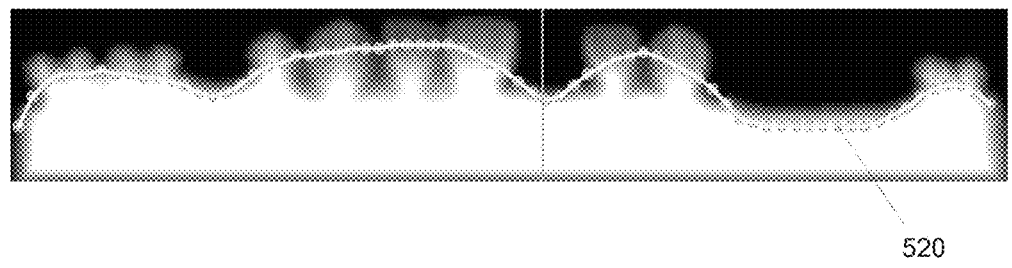
FIG. 5d shows the cut-off line of FIG. 5c after smoothing.

5. As shown in FIG. 5*d*, the cut-off line is smoothed. In one embodiment, a moving average algorithm is used to smooth the cut-off line.
6. The support structure model of FIGS. 3*a* and 3*b* is then modified to have a buccal edge corresponding to the buccal cut-off line.

In a preferred embodiment, the buccal cut-off line is lowered by between 1 mm and 4 mm. It is understood that for an equivalent upper jaw, the buccal cut-off line is raised instead of lowered.

Figure 5E:
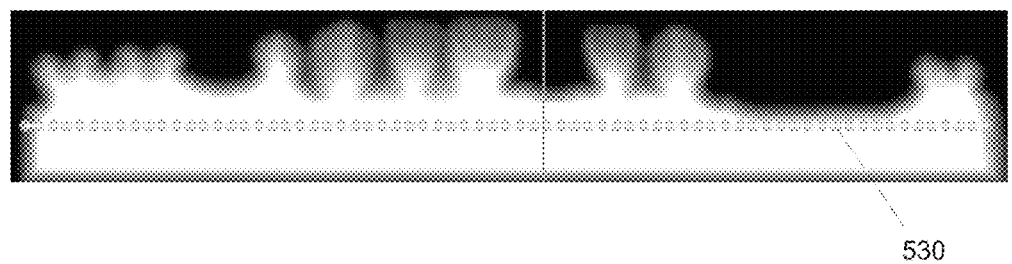
FIG. 5e shows a straight cut-off line used on the lingual side of the support structure.
Figure 5F:
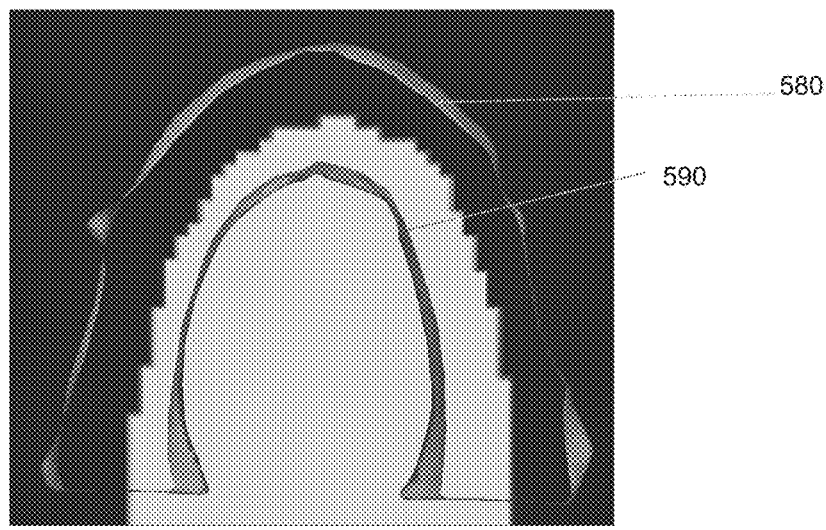
FIG. 5f shows the determination of the buccal or lingual voxel locations on the support structure.

In the preferred embodiment, two cut-off lines are used. On the buccal side, a cut-off line as described above is used. On the lingual side, as shown in FIG. 5*e*, the cut-off line 530 is a straight line at a fixed height. This straight line will result in a larger support structure model at the lingual side providing additional strength. As shown in FIG. 5*f*, in order to automatically determine which side of the support structure model is the buccal side 580 and which side is the lingual side 590, an image is generated from the 3D surface wherein each voxel location is determined to be on the lingual or buccal side. In one embodiment, the step of determining the lingual or buccal side aspect of the voxel is performed by determining at which side of the dental arc the voxel lies.

Figure 6A:
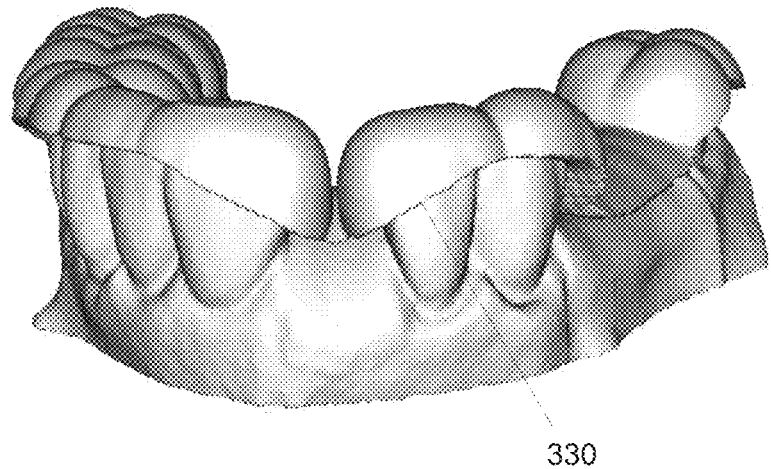
FIG. 6a shows the support structure model of FIG. 3a with an applied cut-off on the buccal side based on the cut-off line of FIG. 5d and cut-off on the lingual side based on the cut-off line of FIG. 5e.
Figure 6B:
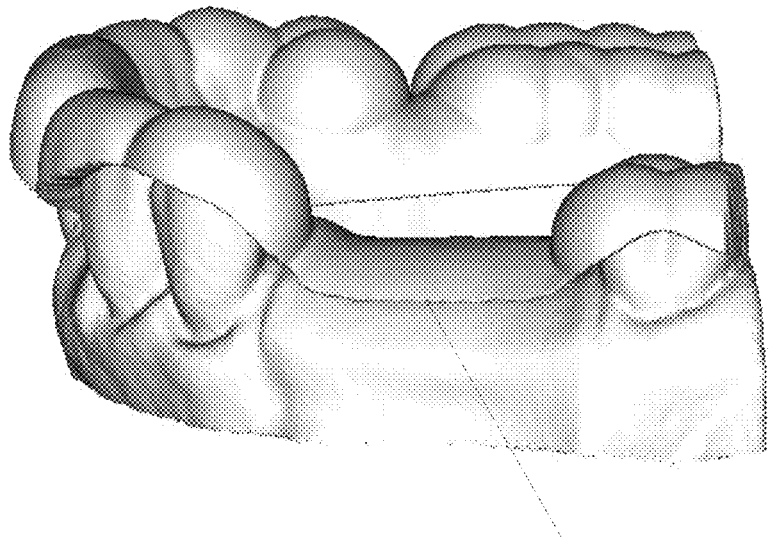
FIG. 6b shows the support structure model of FIG. 6a from a second perspective.

Examples of the resulting support structure model are shown in FIGS. 6*a* and 6*b*.

In one embodiment shown in FIG. 7*a* in which the final surgical template will be supported by anchor pins inserted into the patient's jaw, the cut-off line on the buccal side is modified to provide additional material around the anchor pin sites. In one embodiment as shown in FIG. 7*b*, this is done by lowering the cut-off line to include an area defined by a circle 740 around the anchor pin location site 750 on the panoramic maximum intensity projection of the distance map image. This step is only performed at the side were the anchor pin is located, e.g. the buccal or lingual side.

Figure 8:
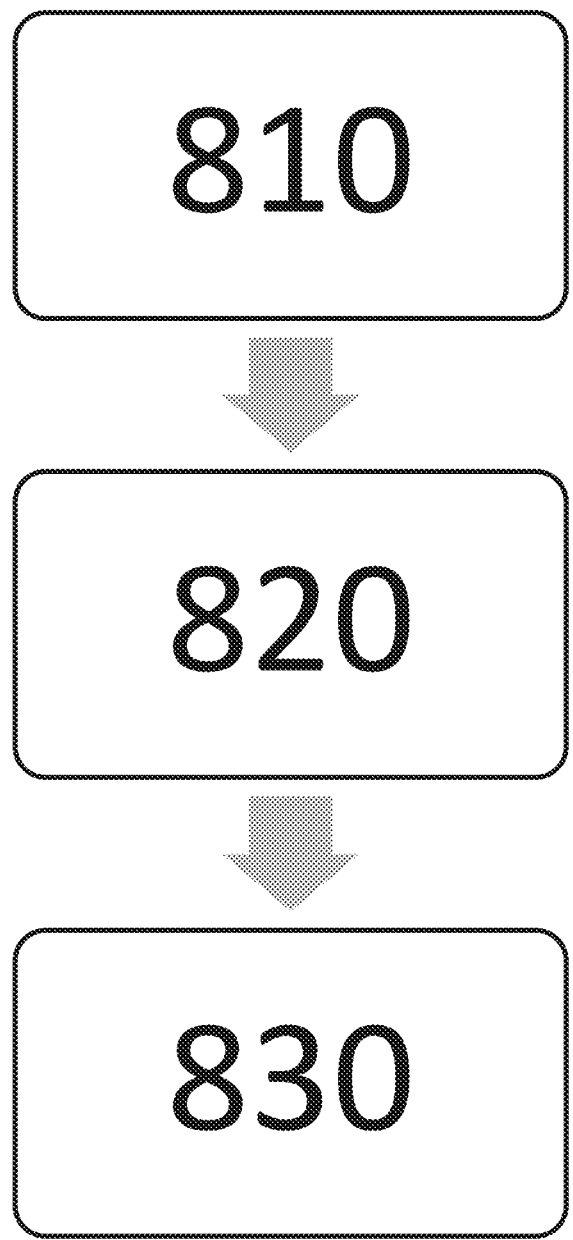
FIG. 8 shows a process flow diagram of the smoothing process for the cut-off line.

In one embodiment shown in FIG. 7*c*, the cut-off line of FIG. 7*b* is smoothed according to the following process shown in FIG. 8:

Shown in step 810, a moving average is calculated along the cut-off line.

In step 820, the curvature of the cut-off line is determined in each recorded point, defining concave and convex parts.

In step 830, only the convex parts of the line are retained for a lower jaw, or only the concave parts are retained for an upper jaw.

A support structure model having a buccal edge based on the unsmoothed cut-off line is shown in FIG. 9*a* and a support structure model having a buccal edge based on the smoothed cut-off line is shown in FIG. 9*b*. The second one is clearly preferable for aesthetic and strength reasons and lowers the risk for hurting the patient.

Support Structure Model Guide Holes

In the preferred embodiment, the support structure model is used to form a surgical template for guiding the drilling of bore holes to allow insertion of oral implants into the patient's jaw bone. Consequently, the support structure model is configured with guide holes. The guide holes may be fitted with matching guide sleeves which typically comprise a harder material and which serve the function of guiding the metal drill guide. As the support structure model material around the guide holes will need to withstand a degree of force from the interaction with the surgeon's tools, the support structure model requires reinforcement for supporting the guide sleeves. The reinforcement is done by adding virtual material to the support structure. Furthermore, the tight fit of the support structure model to the patient's dentition means that the top surface of the support structure model is highly variable.

Figure 10A:
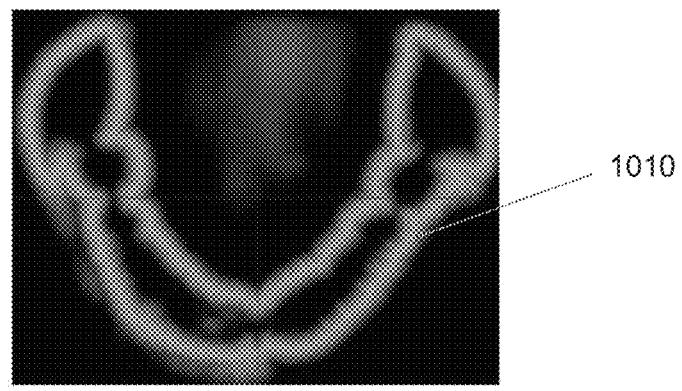
FIG. 10a shows a distance map image of the support structure model of FIG. 10b.
Figure 10B:
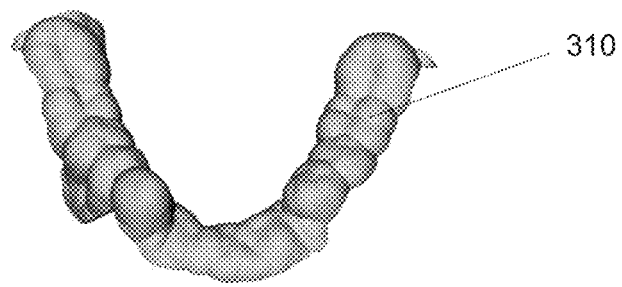
FIG. 10b shows a support structure.
Figure 10C:
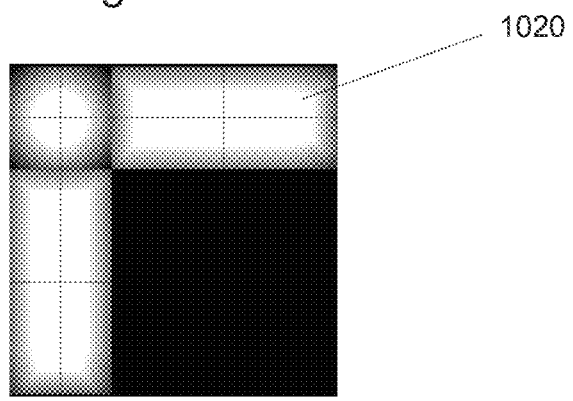
FIG. 10c shows three perspectives of a distance map image of the virtual component of FIG. 10d.
Figure 10D:
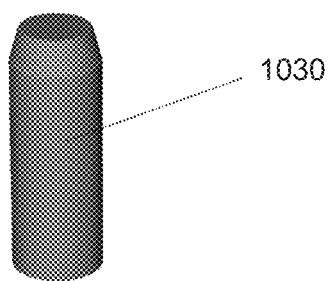
FIG. 10d shows a first virtual component.
Figure 10E:
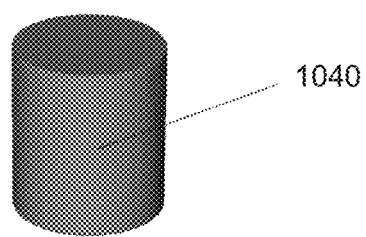
FIG. 10e shows a second virtual component.
Figure 11A:
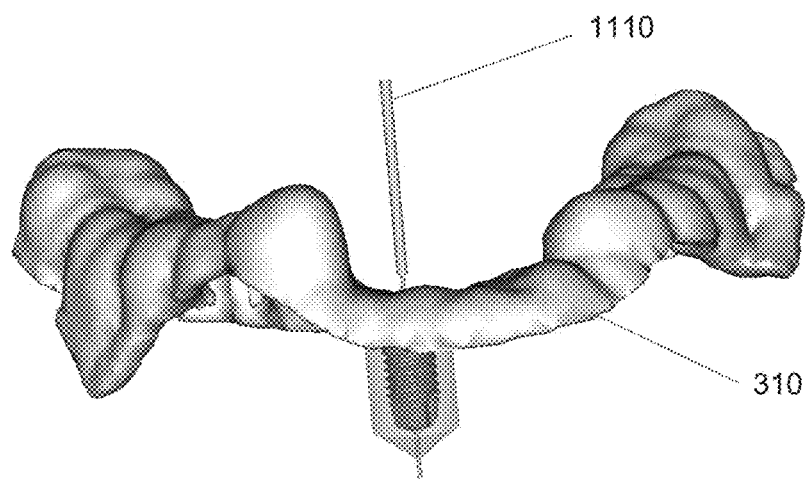
FIG. 11a shows a support structure model before joining the support structure model material and the sleeve support material.
Figure 11B:
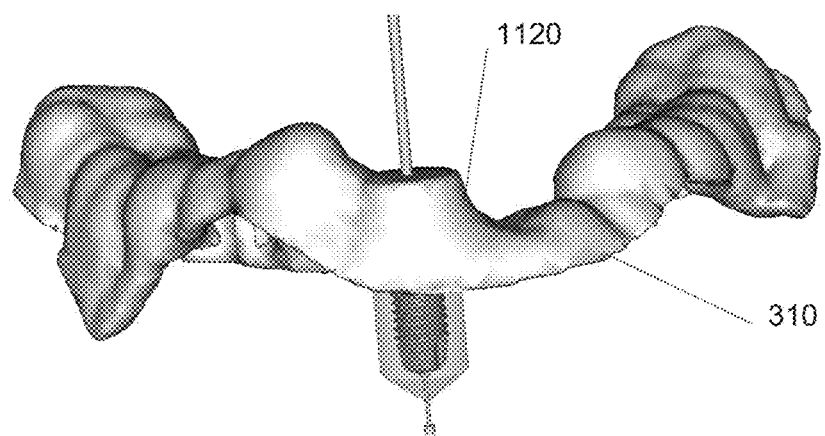
FIG. 11b shows the support structure model of FIG. 11a after the joining of the support structure model material and sleeve support material around a guide hole.
Figure 11C:
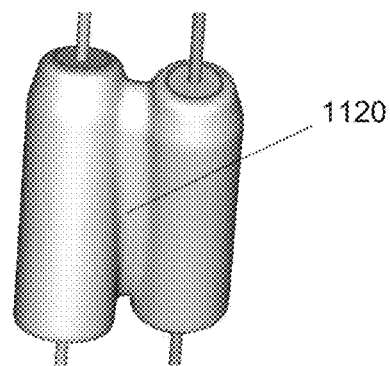
FIG. 11c shows a joining of support material around two proximal guide holes in the support structure.
Figure 11D:
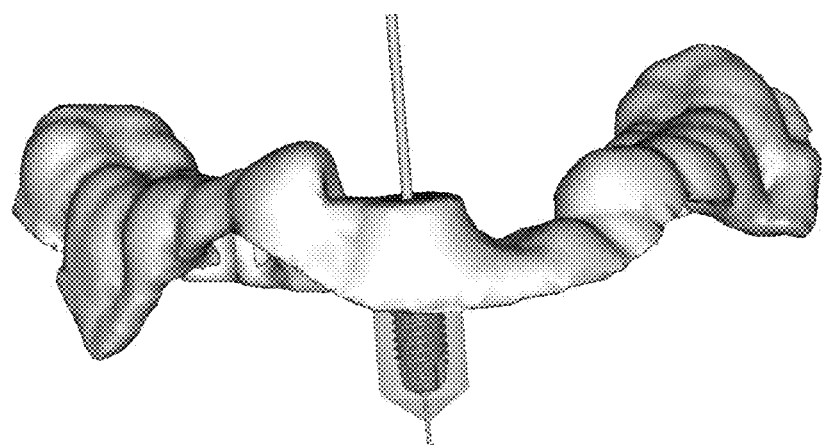
FIG. 11d shows the support structure model of 11b after application of the punch.
Figure 12A:
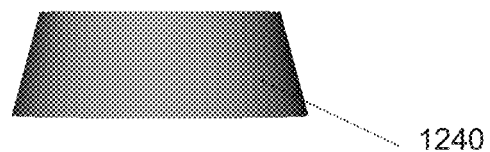
FIGS. 12a-12c show virtual components that are added or subtracted from the support structure model using Boolean operations on the surfaces.
Figure 12B:
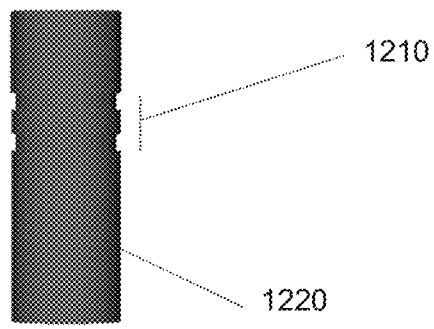
Figure 12C:
Figure 13A:
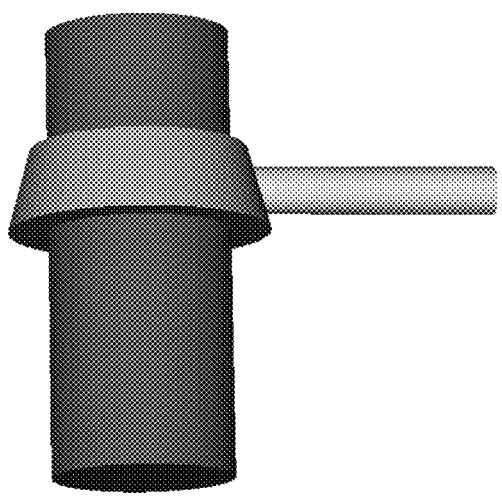
FIG. 13a shows a combination of the virtual components of FIGS. 12a to 12c.
Figure 13B:
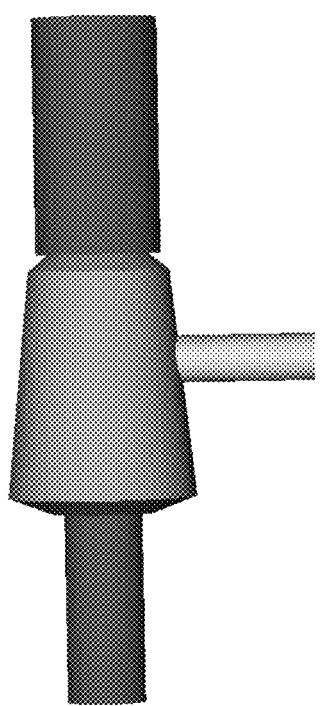
FIG. 13b shows another combination of the virtual components.

For each guide hole, guide sleeve support material is added to the support structure model by:

1. Determining the position of the guide hole in the support structure model in dependence on the intended position of the intending bore hole in the patient's jaw and corresponding installed implant or anchor pin position.
2. Providing a distance map image 1010 (shown in FIG. 10*a*) of the support structure model 310 (an embodiment of which is shown in FIG. 10*b*).
3. Providing a distance map image 1020 (shown in FIG. 10*c*) of a sleeve support shape 1030 (an embodiment of which is shown in FIG. 10*d*).
4. Providing an image of a punch shape 1040 (an embodiment of which is shown in FIG. 10*e*).
5. Overlaying the distance map image of the sleeve support shape onto the distance map image of the support structure model at a position corresponding to the longitudinal axis 1110 of the guide hole in the support structure model and adding support structure model material 1120 where the combined values of the distance map images exceed a threshold. An example of the original support structure model is shown in FIG. 11*a*. An example of the modified support structure model after adding the sleeve support shape is shown in FIG. 11*b*.
6. Where the distance map images of multiple sleeve support shapes overlap, adding support structure model material 1120 where the combined values of the distance map images exceed a threshold. An example of the support structure model material connecting two sleeve support shapes is shown in FIG. 11*c*.
7. Overlaying the image of the punch shape 1040 onto the distance map image of the support structure model at a position corresponding to the top of the guide hole in the support structure model and removing support structure model material at all points within the punch image. An example of the support structure model of FIG. 11*b* after removal of the punch material is shown in FIG. 11*d*.
8. Once all of the above steps have been completed for each of the guide holes, the support structure model image is converted to a 3D surface model. This process may be done using a marching cubes algorithm.
9. After that, a 3D surface model 1240 of the top surface of the sleeve support (FIG. 12*a*) is added again to the support structure model 3D surface model at a position corresponding to the top of the guide hole. This provides a clean and level top surface for the top of the guide hole where it interfaces with a drill guide.
10. Then a 3D surface model of the sleeve support space 1220 (FIG. 12*b*) is subtracted, to provide a hole for drilling and insertion of an implant. The sleeve support space shown in FIG. 12*b* also includes a portion 1210 to provide an interface between the final surgical template and the sleeve and to provide space for glue retention between the two.
11. Finally, a 3D surface of a glue tube 1230 (FIG. 12*c*) is subtracted so that the glue can be inserted in between the final surgical template and the sleeve in order to fix the sleeve to the template.
12. FIG. 13*a* shows all the components of FIGS. 12*a*-12*c* together in one image. FIG. 13*b* shows a collection of equivalent components used to form an anchor pin guide hole in the final surgical template.

13. In order to remove any material added in the above steps to the support structure model which affects the close fit with the teeth, the original 3D surface data of the patient's oral situation is subtracted from the support structure model 3D surface model. In one embodiment, a slightly enlarged 3D surface data of the patient's oral situation is subtracted from the support structure model 3D surface model in order to ensure a small degree of tolerance between the final produced surgical template and the patient's oral situation.

In one embodiment of step 5 or step 6 above, if the combined distances of two points in the distance map images from their respective closest points on the respective surfaces is less than 2 mm, additional support material is added.

This technique for generating guide holes in the support structure model is also applicable to the anchor pin guide holes used by the anchor pins to fix a surgical template to the patient's jawbone.

Lateral Sleeve Openings

In the preferred embodiment of the invention, lateral openings are provided in the support structure. The corresponding opening(s) in the produced dental splint allows the lateral insertion of guide sleeves and/or guide tools (i.e. tools with a component which fits the guide hole opening and provides support for a drill bit or other tool during the surgical procedure) into the guide hole(s). The lateral openings are formed in the support structure model by performing a Boolean subtraction of a box shape from the support structure. The subtraction provides a continuous opening from the guide hole to the external surface of the support structure. The opening begins at the coronal edge of the support structure model and runs parallel to the opening with a height greater, equal to, or shorter than the length of the guide hole. The width in the distal-mesial direction is equal to or slightly smaller than the diameter of the guide hole to provide a retention fit for components in the guide hole. Lateral openings may be provided at either the buccal or lingual side of the support structure, although not both/

In another embodiment, the lateral openings are formed by adjusting the cut-off line to provide a gap in the support structure model at either the buccal or lingual side. In such an embodiment, the same dimensions as described above are used.

Support Structure Model Undercut Removal

Figure 14A:
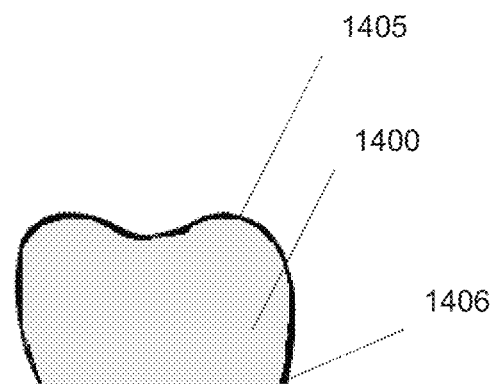
FIG. 14a shows a cross-sectional view of a tooth of the oral situation.
Figure 14B:
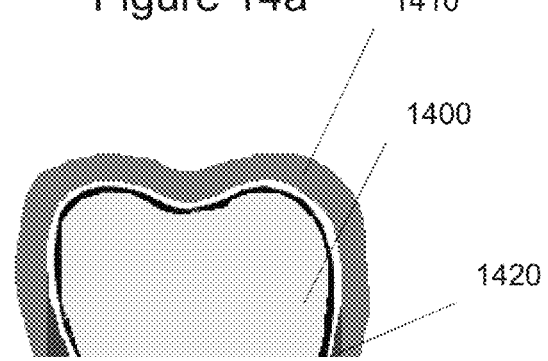
FIG. 14b shows the tooth of FIG. 14a with a support structure model applied and shows a determination of the under-cut voxels to be removed.

In the preferred embodiment, the support structure model is modified to ensure that it can be easily fitted over the patient's dentition. As shown in FIGS. 14*a* and 14*b*, the supporting tooth 1400 is wider at the crown 1405 of the tooth before narrowing towards the neck 1406 and root of the tooth. A support structure model 1410 formed according to the above methods will have a curving shape which matches the shape of the tooth. Consequently, the opening of the support structure model at the cut-off point 1420 could be narrower than the widest point of the tooth. This will make it difficult if not impossible for the dentist to fit a surgical template corresponding to the support structure model without damaging the surgical template.

In the preferred embodiment, the support structure model is modified to remove any part 1420 of the support structure model which forms an undercut. In one embodiment, this is achieved by:

1. Along the arc 410 of the distance map image, the widest point of the teeth of the patient is calculated. The height of this widest point is also determined on the panoramic maximum intensity projection of the distance map image.

Figure 14C:
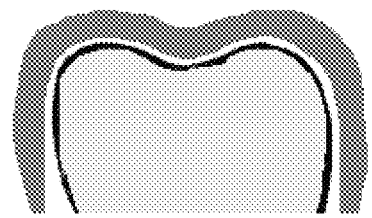
FIG. 14c shows the support structure model of FIG. 14b with the under-cut voxels removed.

2. Any part of the support structure model which is closer to the arc 410 and below the height of the widest point of the teeth is removed as shown in FIG. 14*c*.

Production of the Physical Surgical Template

Finally, a physical surgical template (or dental splint) is produced in dependence on the virtual surgical template model. The physical surgical template may be manufactured using an additive manufacturing technique. The advantage of this technique is the speed with which the physical surgical template can be produced. Preferably, the physical surgical template is produced as a physical reproduction of the virtual surgical template model using stereolithography. Other additive manufacturing technologies that may be used include inkjet 3D printers or SLS printers. Alternatively, the physical reproduction of the virtual surgical template model may be milled from a block of material.

Figure 15:
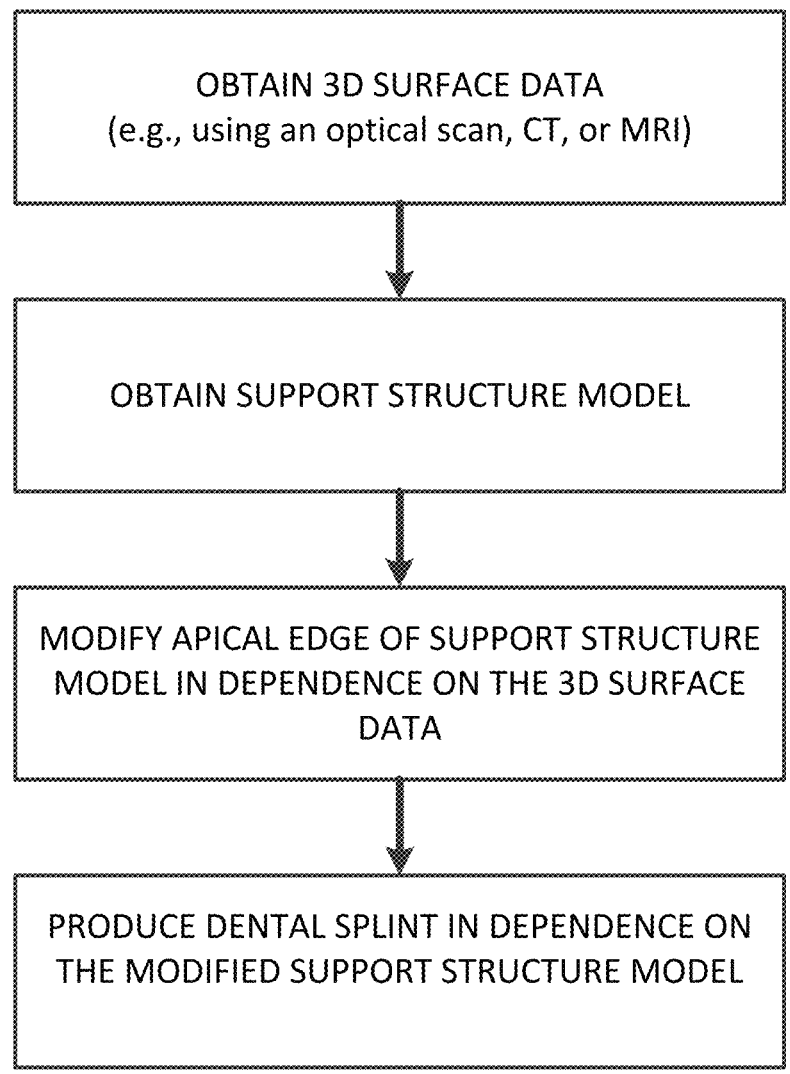
FIG. 15 shows a process flow diagram of an example method of producing a dental splint.

FIG. 15 shows a process flow diagram of an example method of producing a dental splint.

The invention claimed is:

1. A method of producing a dental splint comprising:
    obtaining a set of 3D surface data, the 3D surface data representing a surface of a patient's oral situation,
    obtaining a support structure model describing a component configured to fit to a portion of the surface of the patient's oral situation,
    modifying an apical edge of the support structure model in dependence on the 3D surface data, wherein the apical edge of the support structure model is modified to correspond to a cut-off line generated by a method including:
        generating a 2D panoramic image of the 3D surface data,
        forming a coronal edge line representing the highest points along the top of a coronal edge of the 2D panoramic image, and
        transposing the coronal edge line in an apical direction to form the cut-off line,
    producing the dental splint in dependence on the modified support structure model.

2. The method of claim 1, wherein the 2D panoramic image is a maximum intensity projection image of a 3D distance map image of the 3D surface data, the 3D distance map being a voxel image wherein each voxel in the 3D distance map image has a value corresponding to the distance from said voxel to the closest point on the surface described by the 3D surface data.

3. The method of claim 1, wherein the 2D panoramic image is an orthopantomogram.

4. The method of claim 1, wherein the coronal edge of the 2D panoramic image defines the transition between the representation of patient tissue and empty space.

5. The method of claim 1, wherein the coronal edge line is transposed by between 1 mm and 4 mm in the apical direction to form the cut-off line.

6. The method of claim 1, wherein the cut-off line is smoothed using a smoothing algorithm.

7. The method of claim 1, wherein the cut-off line is smoothed according to a moving averages algorithm.

8. The method of claim 1, wherein only the concave parts of the cut-off line are retained for the upper jaw or only the convex parts of the cut-off line are retained for the lower jaw.

9. The method of claim 1, wherein a determination is made of whether an apical edge of the support structure model is on the lingual or buccal side of the 3D surface data.

10. The method of claim 1, wherein two cut-off lines are determined, the first cut-off line defining the buccal edge of the support structure model and the second cut-off line defining the lingual edge of the support structure model.

11. The method of claim 1, wherein the apical edge of the support structure model on the lingual side of the 3D surface data is a substantially straight line.

12. The method of claim 1, wherein points of the cut-off line are transposed in the apical direction in order to provide support for a lateral hole in the support structure model.

13. The method of claim 1, wherein the support structure model is modified to remove any part forming an undercut.

14. The method of claim 1, wherein the support structure model is a virtual model.

\* \* \* \* \*